US012758123B2

(12) United States Patent
Gebrehiwot

(10) Patent No.: US 12,758,123 B2
(45) Date of Patent: Oct. 13, 2026

(54) METHOD AND APPARATUS FOR USING A BIASED MEMBER TO ASCERTAIN APPROPRIATE STENT SELECTION

(71) Applicant: Boston Scientific Scimed, Inc., Maple Grove, MN (US)

(72) Inventor: Ewnet Gebrehiwot, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 335 days.

(21) Appl. No.: 18/521,705

(22) Filed: Nov. 28, 2023

(65) Prior Publication Data

US 2024/0172961 A1 May 30, 2024

Related U.S. Application Data

(60) Provisional application No. 63/428,636, filed on Nov. 29, 2022.

(51) Int. Cl.

*A61B 5/107* (2006.01)
*A61B 5/02* (2006.01)
*A61B 90/00* (2016.01)

(52) U.S. Cl.

CPC ........ *A61B 5/1076* (2013.01); *A61B 5/02007* (2013.01); *A61B 90/39* (2016.02); *A61B 2090/3925* (2016.02); *A61B 2090/3966* (2016.02)

(58) Field of Classification Search

CPC .................. A61B 5/1076; A61B 90/39; A61B 2090/3904–3995
See application file for complete search history.

(56) References Cited

U.S. PATENT DOCUMENTS 5,238,004 A 8/1993 Sahatjian et al.
6,508,803 B1 1/2003 Horikawa et al.
7,128,736 B1 * 10/2006 Abrams ............. A61B 17/0057 606/1
2005/0010138 A1 * 1/2005 Mangiardi ........... A61B 5/1076 600/587
2011/0213403 A1 * 9/2011 Aboytes ................ A61M 29/02 606/194

(Continued)

FOREIGN PATENT DOCUMENTS

WO WO-0112104 A1 * 2/2001 ............. A61F 2/013
WO WO-2016041961 A2 * 3/2016 ....... A61B 17/12163

*Primary Examiner* — Anh Tuan T Nguyen
*Assistant Examiner* — Younhee Choi
(74) *Attorney, Agent, or Firm* — SEAGER, TUFTE & WICKHEM, LLP

(57) ABSTRACT

An apparatus for determining an effective diameter of a blood vessel at a deployment site includes an outer member defining a garage disposed within the outer member and an inner member slidingly disposed within the garage, the inner member adapted to be advanced distally from the garage in order to obtain or measure a diameter of a blood vessel in which the apparatus is disposed. The inner member includes an elongate shaft and a biased member extending from the elongate shaft, the biased member adapted to extend radially outwardly from the elongate shaft when not constrained by being within the garage. The biased member may be visible via ultrasound imaging and/or fluoroscopic imaging.

16 Claims, 7 Drawing Sheets

(56) References Cited

U.S. PATENT DOCUMENTS

| | | | | |
|---|---|---|---|---|
| 2016/0166257 | A1* | 6/2016 | Allen | A61B 17/12109<br>606/200 |
| 2018/0153555 | A1* | 6/2018 | Herzog | A61B 17/12109 |
| 2019/0133747 | A1* | 5/2019 | Janardhan | A61M 1/742 |
| 2021/0161669 | A1 | 6/2021 | Griffin et al. | |

* cited by examiner

FIG. 1
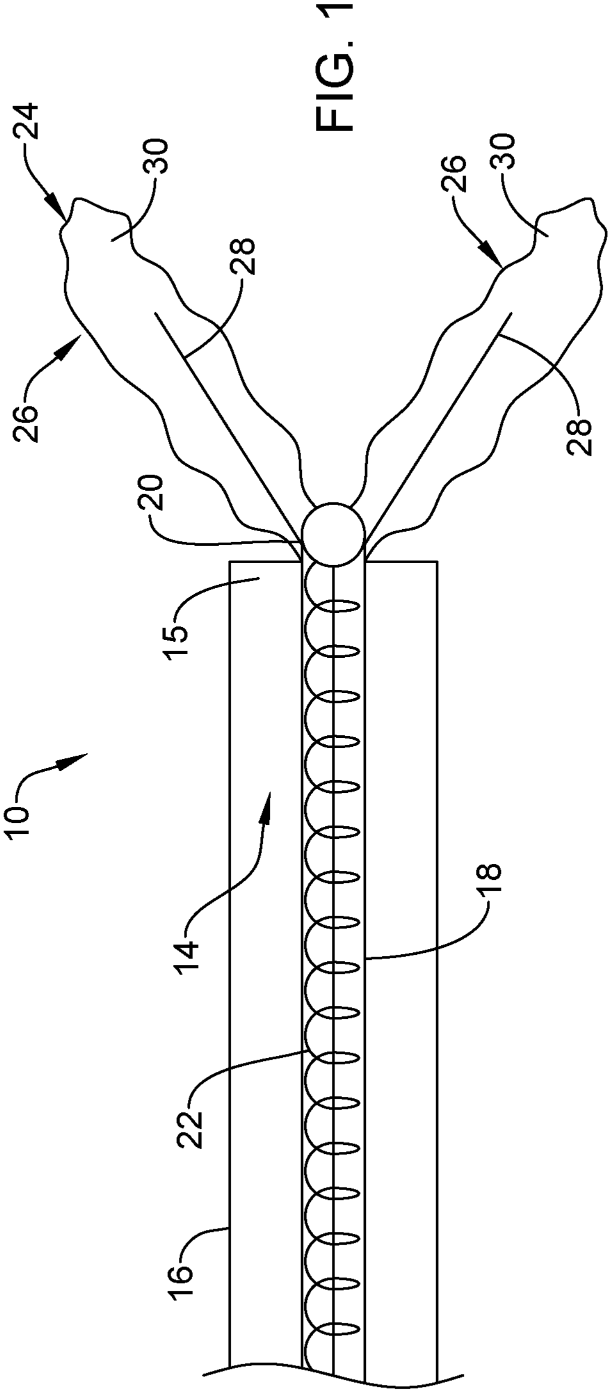
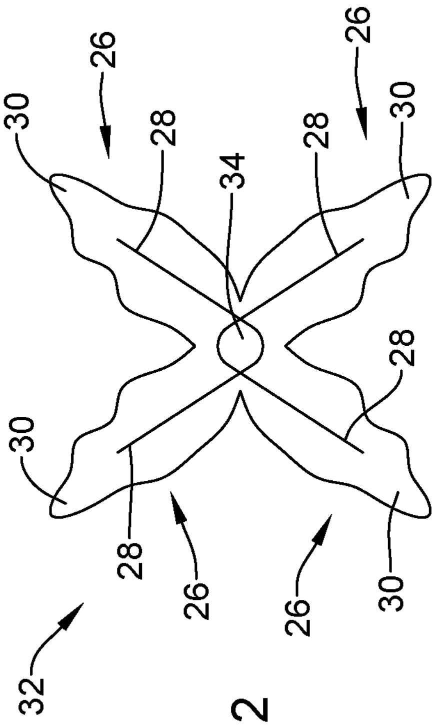
FIG. 2

METHOD AND APPARATUS FOR USING A BIASED MEMBER TO ASCERTAIN APPROPRIATE STENT SELECTION

CROSS-REFERENCE TO RELATED APPLICATIONS

This application claims the benefit of priority under 35 U.S.C. § 119 of U.S. Provisional Application No. 63/428,636, filed Nov. 29, 2022, the entire disclosure of which is hereby incorporated by reference.

TECHNICAL FIELD

The disclosure relates generally to medical devices and more particularly to medical devices that are adapted for use in ascertaining vessel diameter for optimal stent selection.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example may be found in an apparatus for determining an effective diameter of a blood vessel at a deployment site. The apparatus includes an outer member defining a garage disposed within the outer member. An inner member is slidingly disposed within the garage, the inner member adapted to be advanced distally from the garage in order to obtain measure a diameter of a blood vessel in which the apparatus is disposed. The inner member includes an elongate shaft having a distal region, and an expandable member extending from the distal region, the expandable member biased to extend radially outwardly from the distal region when not constrained by being within the garage.

Alternatively or additionally, the expandable member may be adapted to be visible via ultrasound imaging.

Alternatively or additionally, the expandable member may be adapted to be visible via fluoroscopic imaging.

Alternatively or additionally, the expandable member may include a plurality of fingers extending from the distal region of the elongate shaft, each of the plurality of fingers biased to extend radially outwardly from the distal region of the elongate shaft, each of the plurality of fingers constrained from extending radially outwardly when the inner member is disposed within the garage.

Alternatively or additionally, each of the plurality of fingers may include a spring element biased to extend radially outwardly, and a polymeric sleeve extending over the spring element.

Alternatively or additionally, the expandable member may include at least three fingers.

Alternatively or additionally, the expandable member may include at least four fingers.

Alternatively or additionally, the expandable member may include a first grouping of fingers at a first axial position along the elongate shaft, and a second grouping of fingers at a second axial position along the elongate shaft that is spaced apart from the first grouping of fingers.

Alternatively or additionally, the expandable member may include a plurality of spring elements extending from the distal region of the elongate shaft, and a polymeric web enveloping each of the plurality of spring elements.

Alternatively or additionally, the elongate shaft may include a reinforcing element disposed within a polymeric shaft.

Another example may be found in an apparatus for determining an effective diameter of a blood vessel at a deployment site. The apparatus includes an outer member defining a lumen disposed within the outer member, and an inner member slidingly disposed within the lumen, the inner member adapted to be advanced distally from the lumen in order to obtain or measure a diameter of a blood vessel in which the apparatus is disposed. The inner member includes an elongate shaft having a distal region, and a plurality of fingers extending from the distal region of the elongate shaft, each of the plurality of fingers biased to extend radially outwardly from the distal region of the elongate shaft, each of the plurality of fingers constrained from extending radially outwardly when the inner member is disposed within the lumen.

Alternatively or additionally, each of the plurality of fingers may include a spring element biased to extend radially outwardly, and a polymeric sleeve extending over the spring element.

Alternatively or additionally, each of the plurality of fingers may be adapted to be visible via ultrasound imaging.

Alternatively or additionally, each of the plurality of fingers may be adapted to be visible via fluoroscopic imaging.

Alternatively or additionally, the inner member may include at least three fingers.

Alternatively or additionally, the inner member may include at least four fingers.

Alternatively or additionally, the inner member may include a first grouping of fingers at a first axial position along the elongate shaft, and a second grouping of fingers at a second axial position along the elongate shaft that is spaced apart from the first grouping of fingers.

Another example may be found in an apparatus for determining an effective diameter of a blood vessel at a deployment site. The apparatus includes an outer member defining a lumen disposed within the outer member and an inner member slidingly disposed within the lumen, the inner member adapted to be advanced distally from the lumen in order to obtain or measure a diameter of a blood vessel in which the apparatus is disposed. The inner member includes an elongate shaft having a distal region, a plurality of spring elements extending from the distal region of the elongate shaft, and a polymeric web enveloping each of the plurality of spring elements.

Alternatively or additionally, at least a portion of the inner member may be adapted to be visible via ultrasound imaging.

Alternatively or additionally, at least a portion of the inner member may be adapted to be visible via fluoroscopic imaging.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 1 is a schematic view of an illustrative apparatus for determining an effective diameter of a blood vessel with the apparatus shown in an expanded configuration;

FIG. 2 is a schematic end view of an illustrative expandable member that may be used as part of the illustrative apparatus of FIG. 1;

Figure 3:
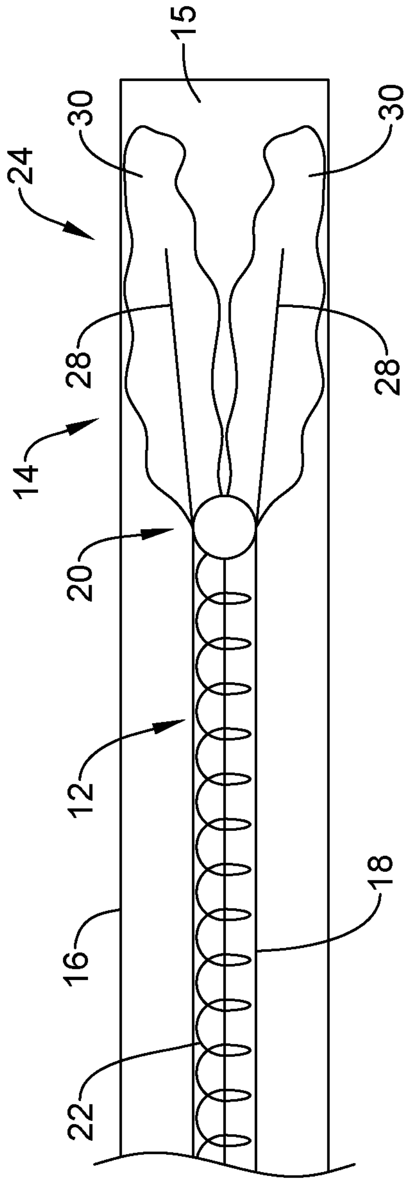
FIG. 3 is a schematic view of the illustrative apparatus of FIG. 1, shown in a collapsed configuration.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Stents are implanted within the vasculature for a variety of reasons. In some cases, an important consideration when selecting a stent for implantation is properly sizing the stent. If the stent is too small, it may not remain in position. If the stent is too large, this can cause a variety of complications. A potential complication in determining an appropriate size for a stent is that the blood vessels such as veins in which the stent is to be deployed can have an irregular cross-sectional shape. Moreover, because the veins function as a capacitive system, the veins can change in size as a result of changes in blood pressure, for example. These factors can make stent sizing more complicated. In some cases, a vein diameter may be estimated by looking at minimum and maximum cross-sectional dimensions, and taking an average as the diameter.

In some cases, a vein diameter may be estimated by treating the vein as having a circular cross-section. For example, a vein diameter may be estimated by determining the cross-sectional area of the vein, and calculating a diameter from the cross-sectional area using the well-known relationship $A=\pi r^2$ (A is area, r is radius). In some cases, a vein diameter may be estimated by determining the perimeter of a cross-section and calculating a diameter from the perimeter using the well-known relationship $P=2\pi r$ (P is perimeter). Each of these methods may provide a different diameter estimate for the same vein. Moreover, each of these methods may not appropriately compensate for phasic or positional changes in diameter, oblong or flattened cross-sections, or errors caused by non-perpendicular measurement planes.

In some cases, an expandable element may be disposed within a vessel to be measured, and the expandable element may be allowed to passively expand until the expandable element contacts the vessel walls and at least partially reshapes the vessel. In some cases, the expandable element may be actively expanded. In either event, the goal is to temporarily reshape the vessel in order to obtain a more accurate vessel diameter, not to excessively stretch or otherwise resize the vessel. An estimated diameter of the vessel may be determined by directly measuring the expanded diameter of the expandable element, by using imaging techniques such as ultrasound, or fluoroscopy in instances in which the expandable element is sufficiently radiopaque. An estimated diameter of the vessel may be determined indirectly, such as by measuring one or more other parameters of the expandable element. In some cases, for example when the expandable element is a braid, there may be known relationships between the diameter of the braid and the length of the braid. This means that for a given change in length, a new diameter can be ascertained. In some cases, changes in braid angle may be used to ascertain how the diameter of the braid has changed as the braid has expanded.

FIG. 1 is a schematic view of an illustrative apparatus 10 that may be used in determining an effective vessel diameter. In this, an effective vessel diameter may be considered as being a diameter that corresponds to the vessel having been at least partially reshaped in the process of making the measurement. The reshaping is considered to be temporary, as the vessel will revert to its native profile once the apparatus 10 has been withdrawn. The effective vessel diameter may be considered as being equivalent to a stent diameter of a stent that is an appropriate size to be deployed at that particular location. The stent should have a diameter that is sufficient to at least partially reshape the vessel when implanted, as this will facilitate the stent remaining in position until such time as tissue ingrowth has further secured the stent in place, without distending the vessel. A guidewire may be advanced through the vasculature until the guidewire reaches and slightly passes a desired stent deployment site. The apparatus 10 may be advanced over the guidewire until the apparatus reaches the desired stent deployment site so that one or more measurements of a vessel's effective diameter may be taken.

The apparatus 10 includes an inner member 12 that is adapted to fit within a garage 14. In some instances, the garage 14 may be considered as being a distal portion of an outer member 16. In some cases, the garage 14 may be considered as being a distal portion of a lumen 15 extending through the elongate member 16. The garage 14 may be considered as being adapted to accommodate the inner member 12 within the garage 14. The inner member 12 may be held within the garage 14 while the apparatus 10 is advanced to a desired location, and then the inner member 12 may be advanced out of the garage 14. Subsequently, the inner member 12 may be retrieved back into the garage 14.

The outer member 16 may be an elongate shaft, for example. The outer member 16 may be a polymeric sheath, and may or may not include any reinforcing members disposed within or about the outer member 16. The inner member 12 includes an elongate shaft 18 that extends proximally from a distal region 20. In some cases, the elongate shaft 18 may extend proximally to a handle position (not shown) that enables a user to translate the elongate shaft 18, and hence the inner member 12, distally relative to the garage 14 in order to deploy the inner member 12, and proximally relative to the garage 14 in order to re-sheath the inner member 12. In some cases, the outer member 16 may additionally or alternatively extend proximally to a handle position such that the outer member 16 may be translated relative to the inner member 12.

In some cases, the elongate shaft 18 may include a reinforcing member 22 in order to increase pushability and/or torqueability of the inner member 12. If included, the reinforcing member 22 may be a coil or a braid, for example. In some cases, the reinforcing member 22 may be a core wire and/or a coil surrounding a core wire, for example. In some cases, the elongate shaft 18 may itself be a hypotube that has been laser cut to provide additional flexibility while maintaining pushability and/or torqueability. In such cases, the elongate shaft 18 would not separately include a reinforcing feature such as the reinforcing member 22.

The inner member 12 also includes an expandable member 24 that is secured to the elongate shaft 18 at or near the distal region 20 of the elongate shaft 18. In some cases, the expandable member 24 may be biased into a position (as shown) in which the expandable member 24 extends radially outwardly from the distal region 20 when the expandable member 24 is not constrained by being in the garage 14. In some cases, the expandable member 24 may be adapted to be visible via ultrasound imaging. In some cases, the expandable member 24 may be adapted to be visible via fluoroscopic imaging. When not constrained by the garage 14, the expandable member 24 may expand into contact with the vessel walls of the vessel in which the inner member 12 is deployed. In some instances, the expandable member 24 may push against the vessel walls with sufficient force to at least partially and temporarily reshape the vessel into a profile that is closer to a circular cross-sectional profile. In some cases, the expandable member 24 may be adapted to push against the vessel walls with sufficient force to temporarily reshape the vessel into a more round profile but not push against the vessel with enough force to cause stretching of the vessel walls.

Once the inner member 12 has been deployed and has sufficiently reshaped the vessel, an appropriate imaging technique may be used to ascertain an outer diameter of the expandable member 24, and thus ascertain an effective diameter of the vessel. After measuring the effective diameter, the inner member 12 may be retracted back into the garage 14 by withdrawing the elongate shaft 18 proximally (or holding the elongate shaft 18 in place and advancing the outer member 16 distally).

As shown, the expandable member 24 includes a plurality of fingers 26 that extend outwardly from the distal region 20 of the elongate shaft 18. Each of the plurality of fingers 26 are biased to extend radially outwardly from the distal region 20 of the elongate shaft 18. It will be appreciated that each of the plurality of fingers 26 may be constrained from extending radially outwardly when the inner member 12 is disposed within the garage 14. The expandable member 24 may include any number of fingers 26. As shown in FIG. 1, the expandable member 24 may include a total of two fingers 26. In some cases, the expandable member 24 may include three fingers 26. The expandable member 24 may include four or more fingers 26, for example.

Each of the fingers 26 may include a spring element 28 that is biased to extend radially outwardly and a polymeric sleeve 30 that extends over the spring element 28. In some cases, at least some of the spring elements 28 may extend proximally into the elongate shaft 18 and thus may help to form at least some of the reinforcing member 22. The spring elements 28 may be formed of any suitable material that can have a remembered shape. For example, the spring elements 28 may be formed of NITINOL or another shape memory material. As another example, the spring elements 28 may be formed of spring steel. It will be appreciated that in some cases the spring elements 28 may be visible under fluoroscopy. While the spring elements 28 are shown as stopping short of an end of the polymeric sleeves 30, in some cases, the spring elements 28 may extend to an end of the polymeric sleeves 30.

The polymeric sleeves 30 may be formed of any suitable polymeric material. In some cases, the polymeric sleeves 30 may be formed of any polymeric material that is soft enough to deform when contacting the vessel wall and to protect the vessel wall from coming into contact with the spring elements 28. As an example, the polymeric sleeves 30 may be formed of a polymer having a durometer in a range of 20 A to 50 A. In some cases, the polymeric sleeves 30 may themselves be sufficiently radiopaque to be visible under fluoroscopy. The polymeric sleeves 30 may be formed of a polymer that is doped with or otherwise includes a radiopaque material such as gold, platinum, palladium, tantalum, tungsten alloy, barium sulfate, and the like. In some cases, the polymeric sleeves 30 may be formed of a polymer that is sufficiently soft that any biasing force provided by the spring elements 28 is enough to bias the entire finger 26 (spring element 28 and polymeric sleeve 30) in a radially outward direction.

FIG. 2 is a schematic end view of an illustrative expandable member 32 that may be used in combination with the inner member 12. The expandable member 32 includes a mid-point 34 where the expandable member 32 may be secured relative to the distal region 20 of the elongate shaft 18 (FIG. 1). The expandable member 32 includes a total of four fingers 26, with each of the fingers 26 including both the spring element 28 and the polymeric sleeve 30.

FIG. 3 is a schematic view of the apparatus 10 shown in a retracted position within the garage 14. In some cases, this represents the apparatus 10 in a configuration for advancing through the vasculature. The inner member 12 has been withdrawn proximally relative to the outer member 16 such that the expandable member 24 is positioned within the garage 14. The garage 14 constrains the expandable member 24 from expanding radially outwardly beyond the walls of the garage 14.

Figure 4:
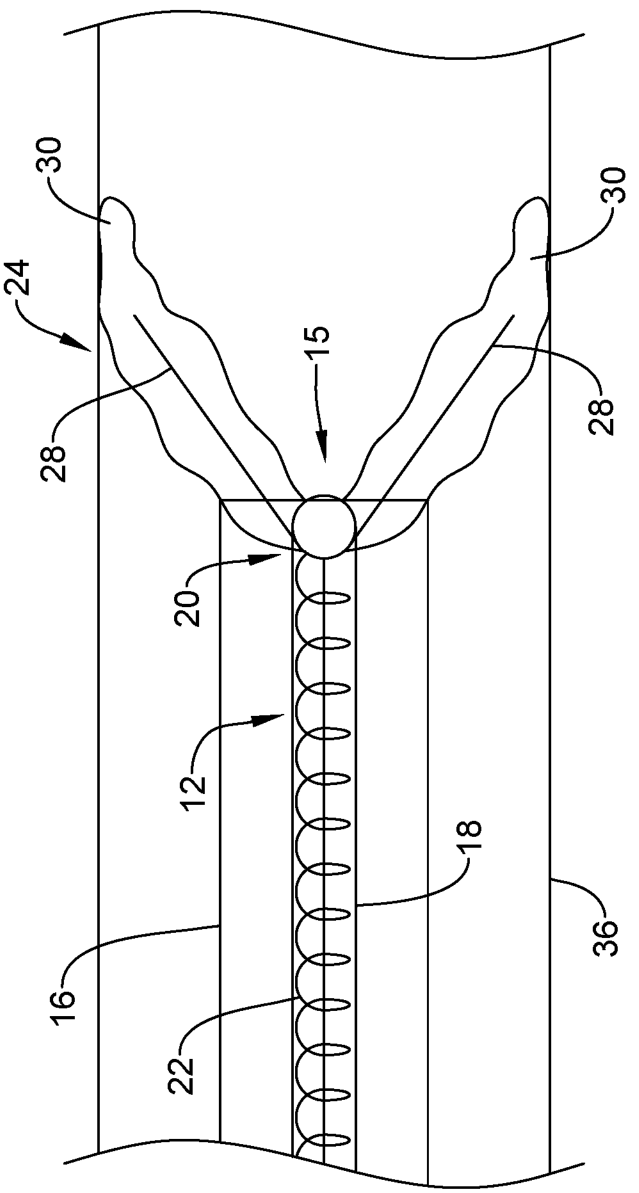
FIG. 4 is a schematic view of the illustrative apparatus of FIG. 1, shown in position within a blood vessel for ascertaining an effective vessel diameter of the blood vessel.

FIG. 4 is a schematic view of the apparatus 10 shown in an extended position in which the expandable member 24 has exited the garage 14. The apparatus 10 is shown within a vessel 36. In some cases, as shown, the polymeric sleeves 30 may deform where the polymeric sleeves 30 contact walls of the vessel 36. In some cases, this deformation helps to reduce the forces that would otherwise be applied to the walls of the vessel 36 by the spring elements 28. In order to ascertain an effective diameter of the vessel 36 at the location shown, the spacing between the polymeric sleeves 30 may be measured using either ultrasound imaging or fluoroscopy.

Figure 5:
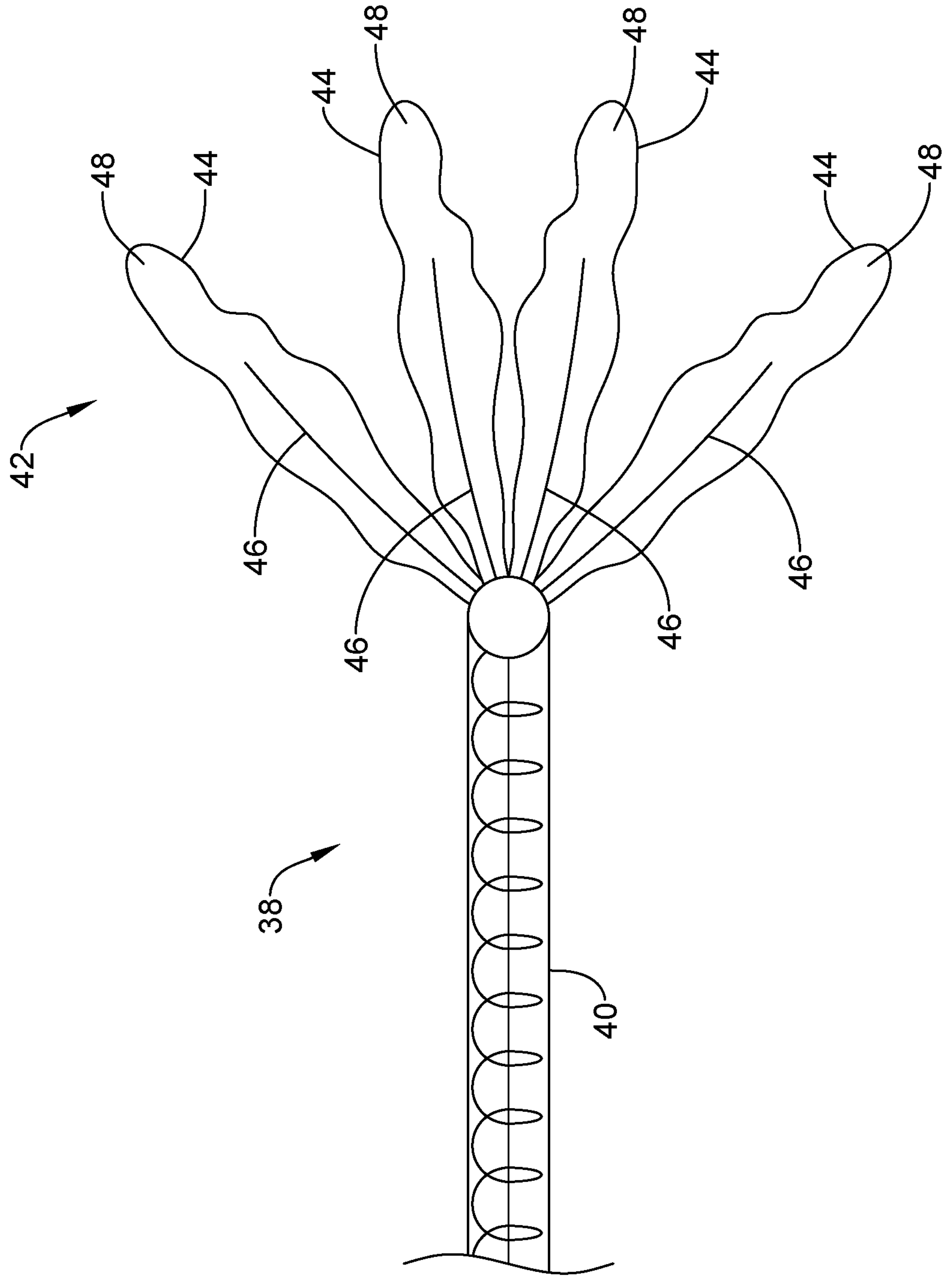
FIG. 5 is a schematic view of an illustrative inner member.
Figure 6:
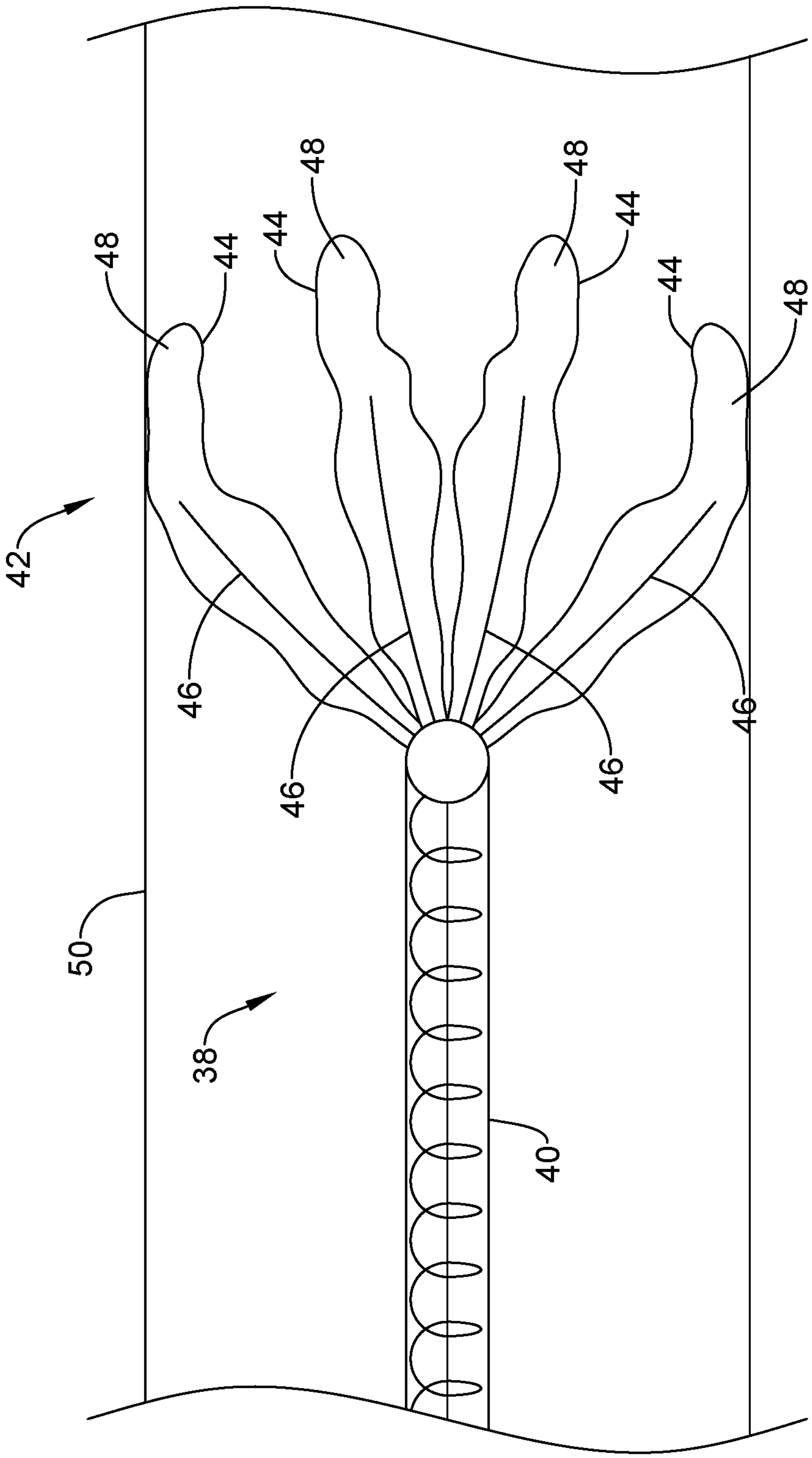
FIG. 6 is a schematic view of the illustrative inner member of FIG. 5, shown in position within a blood vessel for ascertaining an effective vessel diameter of the blood vessel.

FIG. 5 is a schematic view of an inner member 38 that may be used in place of the inner member 12 (FIG. 1). The inner member 38 includes an elongate shaft 40 and an expandable member 42 that is secured relative to the elongate shaft 40. The expandable member 42 includes a total of four fingers 44, with each finger 44 including a spring element 46 that is disposed within a corresponding polymeric sleeve 48. FIG. 6 shows the inner member 38 within a blood vessel 50. As can be seen, in some cases, at least some of the fingers 44 deform in response to contact with the blood vessel 50. Once positioned as shown, an effective diameter of the blood vessel 50 may be ascertained by measuring the spacing between the polymeric sleeves 48 using either ultrasound imaging or fluoroscopy.

Figure 7:
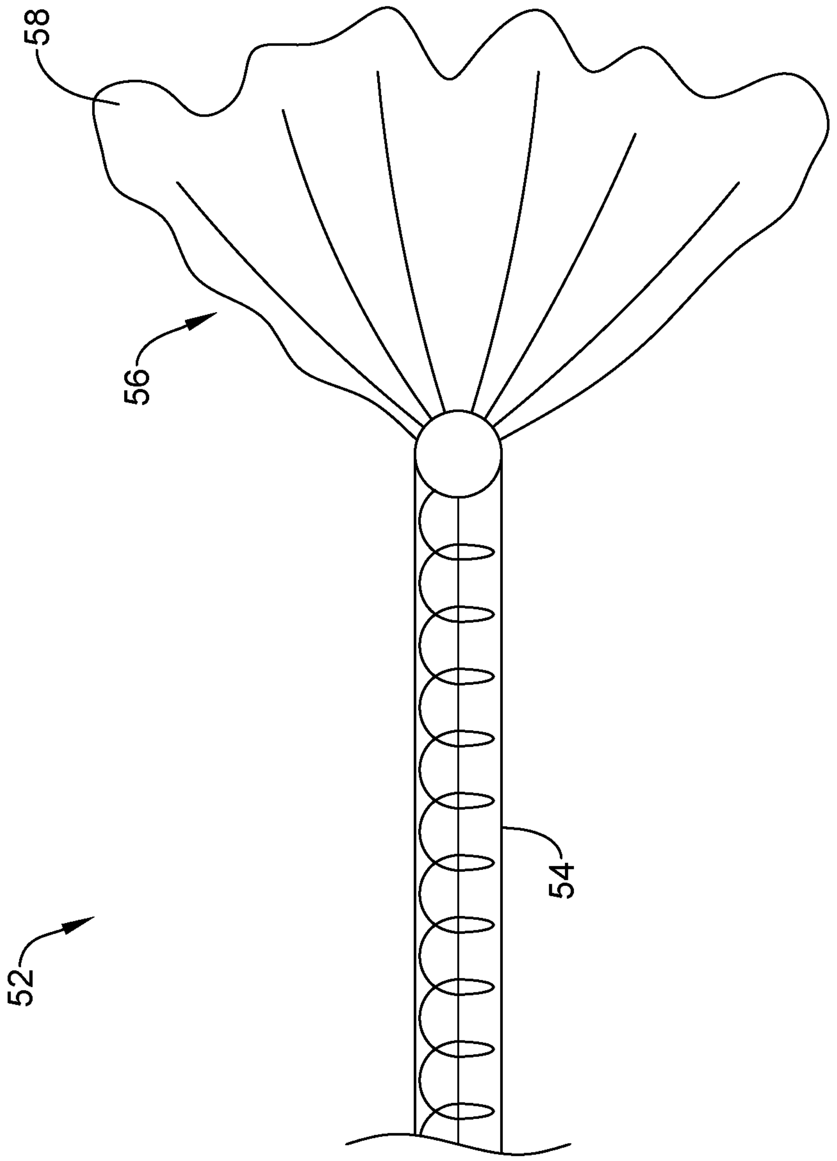
FIG. 7 is a schematic view of an illustrative inner member.
Figure 8:
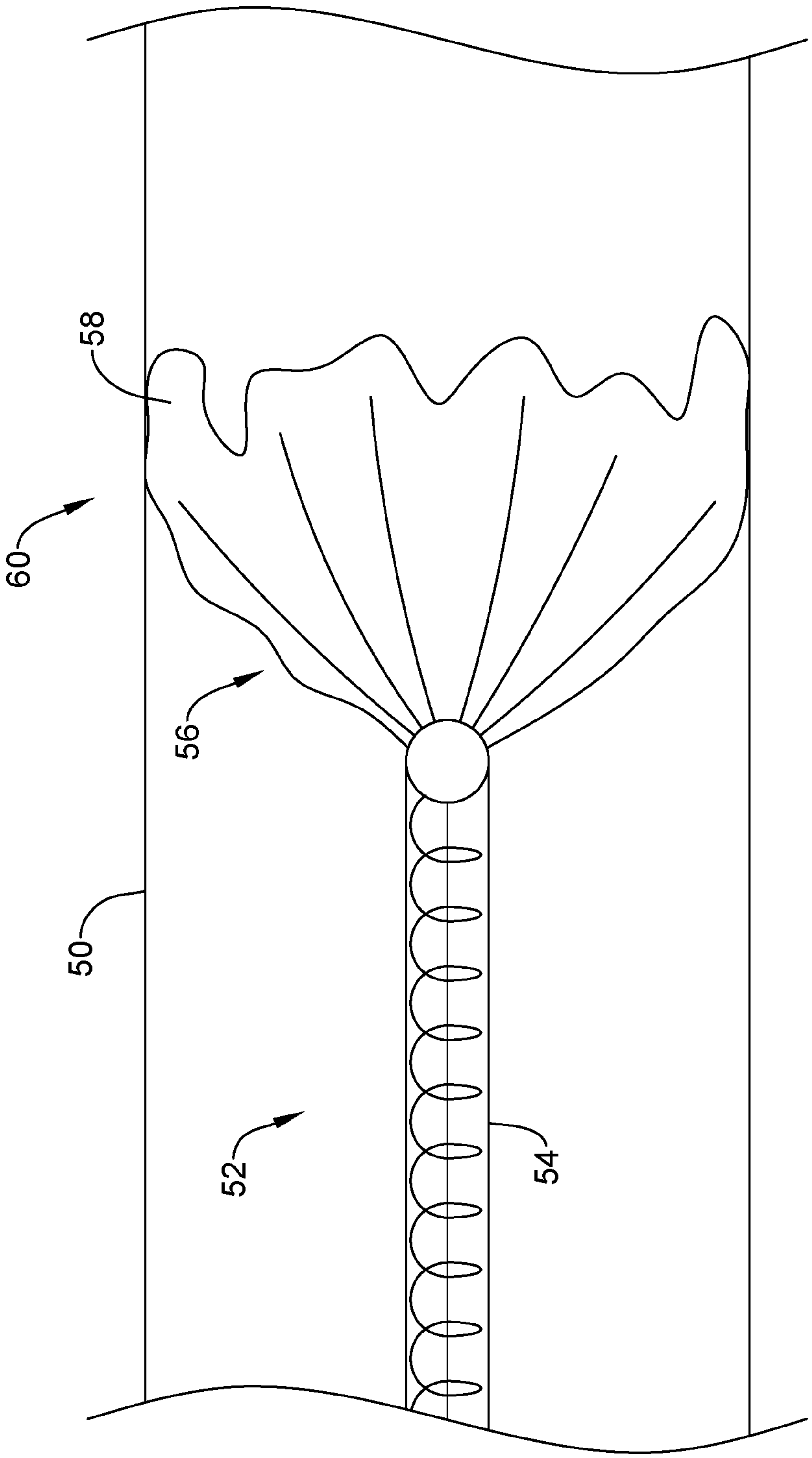
FIG. 8 is a schematic view of the illustrative inner member of FIG. 7, shown in position within a blood vessel for ascertaining an effective vessel diameter of the blood vessel.

FIG. 7 is a schematic view of an inner member 52 that may be used in place of the inner member 12 (FIG. 1). The inner member 52 includes an elongate shaft 54 and an expandable member 56 that is secured relative to the elongate shaft 54. Rather than including a number of distinct fingers, the expandable member 56 includes a polymeric web 58 and a number of spring elements 58 that are disposed within the polymeric web 58. FIG. 8 shows the inner member 52 within the blood vessel 50. As can be seen, in some cases, portions of the polymeric web 58 deform in response to contact with the blood vessel 50. Once positioned as shown, an effective diameter of the blood vessel 50 may be ascertained by measuring an overall diameter of the polymeric web 58 using either ultrasound imaging or fluoroscopy.

Figure 9:
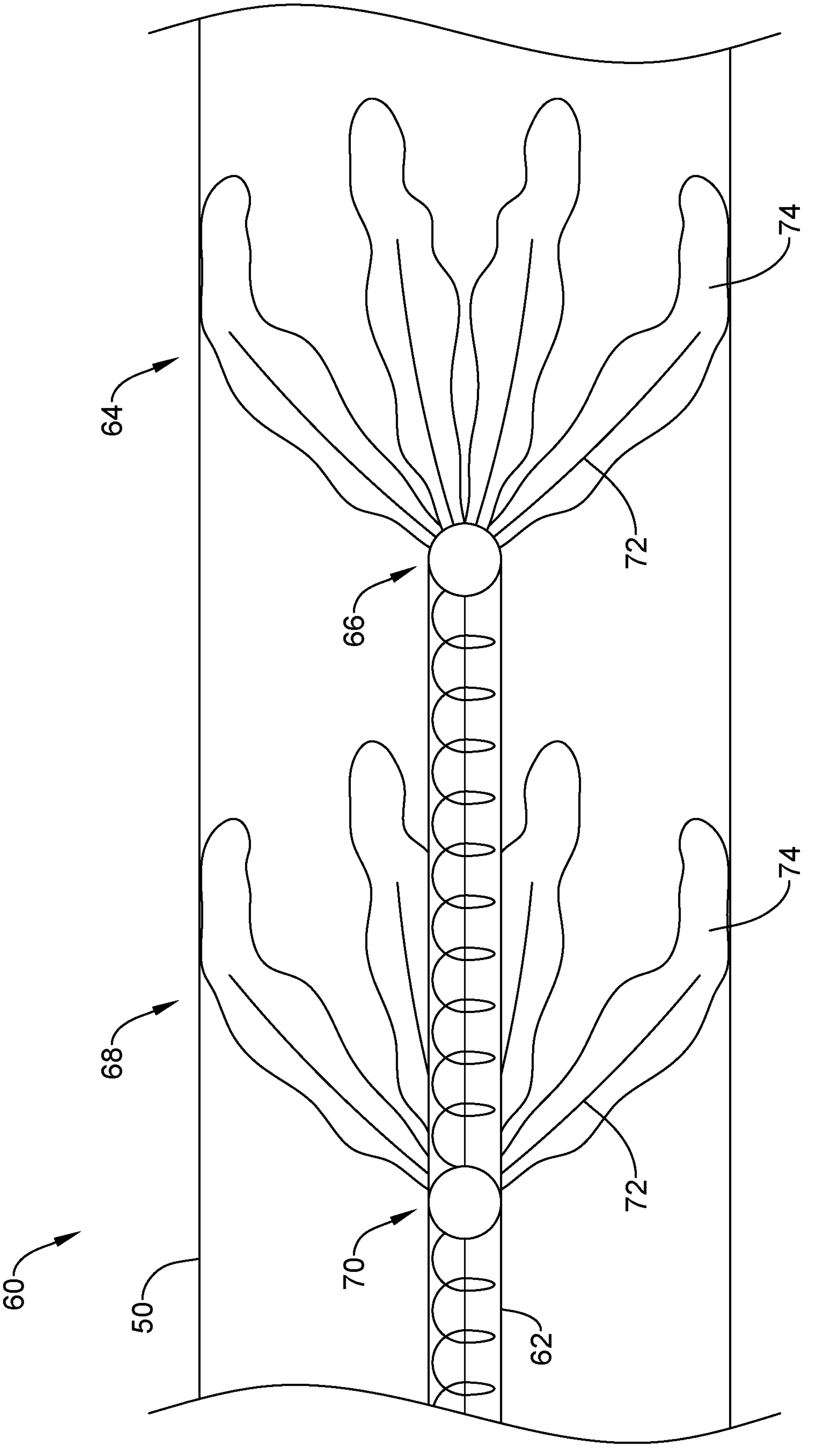
FIG. 9 is a schematic view of an illustrative inner member shown in position within a blood vessel for ascertaining an effective vessel diameter of the blood vessel.

FIG. 9 is a schematic view of an inner member 60 that may be used in place of the inner member 12 (FIG. 1). The inner member 60 is shown in place within the blood vessel 50. The inner member 60 includes an elongate shaft 62. The inner member 60 includes a first grouping 64 of fingers that are secured to the elongate shaft 62 at a first axial position 66 and a second grouping 68 of fingers that are secured to the elongate shaft 62 at a second axial position 70. The second axial position 70 is spaced apart from the first axial position 66. Each of the fingers within the first grouping 64 of fingers and within the second grouping 68 of fingers may include a spring element 72 disposed within a corresponding polymeric sleeve 74. In some cases, an ultrasound catheter such as an IVUS® catheter or an ICE catheter may be inserted parallel to the inner member 60 in order to take dimensional measurements either between the first grouping 64 of fingers and the second grouping 68 of fingers, or distal of the first grouping 64 of fingers.

The materials that can be used for the devices described herein may include those commonly associated with medical devices. The devices described herein, or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V. 304L, and 316LV stainless steel; mild steel; nickel-titanium alloy such as linear-clastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super clastic varieties, may exhibit distinct and useful mechanical properties. Linear elastic and/or non-super-elastic nitinol may be distinguished from super-elastic nitinol in that the linear elastic and/or non-super-elastic nitinol does not display a substantial "superelastic plateau" or "flag region" in its stress/strain curve like super-elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super-elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, the devices described herein, or components thereof, may also be doped with, made of, or otherwise include a radiopaque material. Radiopaque materials are understood to be materials capable of producing a relatively bright image on a fluoroscopy screen or another imaging technique during a medical procedure. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MRI) compatibility is imparted into the devices described herein, or components thereof. For example, The devices described herein, or components thereof, may be made of a material that does not substantially distort the image and create substantial artifacts (e.g., gaps in the image). Certain ferromagnetic materials, for example, may not be suitable because they may create artifacts in an MRI image. The devices described herein, or components thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of the devices described herein in order to define a generally smooth outer surface. In other embodiments, however, such a sheath or covering may be absent. The sheath may be made from a polymer or other suitable material. Some examples of suitable polymers may include polytetrafluoroethylene (PTFE), cthylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the devices described herein may be sandblasted, beadblasted, sodium bicarbonate-blasted, electropolished, etc. In these as well as in some other embodiments, a coating, for example a lubricious, a hydrophilic, a protective, or other type of coating may be applied. Alternatively, a sheath may include a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

Portions of the devices described herein may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present disclosure.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An apparatus for determining an effective diameter of a blood vessel at a deployment site, the apparatus comprising:

an outer member defining a garage disposed within the outer member; and an inner member slidingly disposed within the garage, the inner member adapted to be advanced distally from the garage in order to determine the effective diameter of the blood vessel in which the apparatus is disposed, the inner member comprising:

an elongate shaft having a distal region; and an expandable member extending from the distal region, the expandable member biased to extend radially outwardly from the distal region when not constrained by being within the garage;

wherein the expandable member comprises:

a first group of fingers at a first axial position along the elongate shaft, each finger of the first group of fingers including a spring element disposed within a distinct polymeric sleeve; and a second group of fingers at a second axial position along the elongate shaft, each finger of the second group of fingers including a spring element disposed within a distinct polymeric sleeve.

2. The apparatus of claim 1, wherein the expandable member is adapted to be visible via ultrasound imaging.

3. The apparatus of claim 1, wherein the expandable member is adapted to be visible via fluoroscopic imaging.

4. The apparatus of claim 1, wherein each finger of the first plurality of fingers and each finger of the second plurality of fingers are biased to extend radially outwardly from the distal region of the elongate shaft.

5. The apparatus of claim 1, wherein each spring element of the first plurality of fingers and the second plurality of fingers is biased to extend radially outwardly.

6. The apparatus of claim 4, wherein the first plurality of fingers comprise at least three fingers.

7. The apparatus of claim 4, wherein the first plurality of fingers comprise at least four fingers.

8. The apparatus of claim 1, wherein the second plurality of fingers comprise at least three fingers.

9. The apparatus of claim 1, wherein the second plurality of fingers comprise at least four fingers.

10. The apparatus of claim 1, wherein the elongate shaft comprises a polymeric shaft with a reinforcing element disposed within the polymeric shaft.

11. An apparatus for determining an effective diameter of a blood vessel at a deployment site, the apparatus comprising:

an outer member defining a lumen disposed within the outer member; and an inner member slidingly disposed within the lumen, the inner member adapted to be advanced distally from the lumen in order to determine the effective diameter of the blood vessel in which the apparatus is disposed, the inner member comprising:

an elongate shaft having a distal region; and a plurality of fingers extending from the distal region of the elongate shaft, each of the plurality of fingers biased to independently extend radially outwardly from the distal region of the elongate shaft, each of the plurality of fingers constrained from extending radially outwardly when the inner member is disposed within the lumen, wherein each of the plurality of fingers comprises:

a spring element biased to extend radially outwardly; and a separate polymeric sleeve extending over the spring element.

12. The apparatus of claim 11, wherein each of the plurality of fingers are adapted to be visible via ultrasound imaging.

13. The apparatus of claim 11, wherein each of the plurality of fingers are adapted to be visible via fluoroscopic imaging.

14. The apparatus of claim 11, wherein the plurality of fingers comprise at least three fingers.

15. The apparatus of claim 11, wherein the plurality of fingers comprise at least four fingers.

16. The apparatus of claim 11, wherein the plurality of fingers comprise:

a first grouping of fingers at a first axial position along the elongate shaft; and a second grouping of fingers at a second axial position along the elongate shaft that is spaced apart from the first grouping of fingers.

* * * * *